US008530422B2

(12) United States Patent
Chen et al.

(10) Patent No.: US 8,530,422 B2
(45) Date of Patent: Sep. 10, 2013

(54) CHIMERIC AQUARETIC AND NATRIURETIC POLYPEPTIDES LACKING VASODILATORY ACTIVITY

(75) Inventors: Horng H. Chen, Rochester, MN (US); John C. Burnett, Jr., Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/592,819

(22) Filed: Aug. 23, 2012

(65) Prior Publication Data

US 2013/0023478 A1 Jan. 24, 2013

Related U.S. Application Data

(62) Division of application No. 12/440,053, filed as application No. PCT/US2007/077900 on Sep. 7, 2007, now Pat. No. 8,283,318.

(60) Provisional application No. 60/825,028, filed on Sep. 8, 2006.

(51) Int. Cl.
*C07K 14/00* (2006.01)

(52) U.S. Cl.
USPC ...... 514/12.4; 536/23.4; 530/324; 435/252.3; 424/93.21

(58) Field of Classification Search
None
See application file for complete search history.

(56) References Cited

U.S. PATENT DOCUMENTS

| | | | |
|---|---|---|---|
| 4,034,074 A | 7/1977 | Miles | |
| 4,098,876 A | 7/1978 | Piasio et al. | |
| 4,233,402 A | 11/1980 | Maggio et al. | |
| 5,296,347 A | 3/1994 | LaMotte, III | |
| 5,449,662 A | 9/1995 | Scarborough | |
| 5,580,859 A | 12/1996 | Felgner et al. | |
| 5,583,108 A | 12/1996 | Wei et al. | |
| 5,589,466 A | 12/1996 | Felgner et al. | |
| 6,407,211 B1 | 6/2002 | Burnett et al. | |
| 6,818,619 B2 | 11/2004 | Burnett et al. | |
| 7,384,917 B2 | 6/2008 | Burnett et al. | |
| 2006/0183154 A1 | 8/2006 | Shih et al. | |
| 2007/0281887 A1 | 12/2007 | Pan | |

FOREIGN PATENT DOCUMENTS

| | | |
|---|---|---|
| WO | WO 89/09611 | 10/1989 |
| WO | WO 2004/047871 | 6/2004 |
| WO | WO 2005/072055 | 8/2005 |

OTHER PUBLICATIONS

Chaurand et al., "Peptide and protein identification by matrix-assisted laser desorption ionization (MALDI) and MALDI-post-source decay time-of-flight mass spectrometry," *J. Am. Soc. Mass Spectrom.*, 1999, 10(2):91-103.

Chen et al., "Equimolar doses of atrial and brain natriuretic peptides and urodilatin have differential renal actions in overt experimental heart failure," *Am. J. Physiol. Regul. Integr. Comp. Physiol.*, 2005, 288:R1093-R1097

Chen et al., "Renal response to acute neutral endopeptidase inhibition in mild and severe experimental heart failure," *Circulation*, 1999, 100:2443-2448.

Cole et al., "The EBV-Hybridoma technique and its application to human lung cancer," *Monoclonal Antibodies and Cancer Therapy*, 1985, Alan R. Liss, Inc., pp. 77-96.

Cote et al., "Generation of human monoclonal antibodies reactive with cellular antigens," *Proc. Natl. Acad. Sci. USA*, 1983, 80:2026-2030.

Gevaert et al., "Protein identification based on matrix assisted laser desorption/ionization-post source decay-mass spectrometry," *Electrophoresis*, 2001, 22(9):1645-1651.

Guatelli et al., "Isothermal in vitro amplification of nucleic acids by a multienzyme reaction modeled after retroviral replication," *Proc. Natl. Acad. Sci. USA*, 1990, 87:1874-1878.

Haber et al., "Application of a radioimmunoassay for angiotensin I to the physiologic measurements of plasma renin activity in normal human subjects," *J. Clin. Endocrinol.*, 1969, 29:1349-1355.

Huse et al., "Generation of a large combinatorial library of the immunoglobulin repertoire in phage lambda," *Science*, 1989, 246:1275-1281.

Hyrup et al., "Peptide nucleic acids (PNA): Synthesis, properties and potential applications," *Bioorgan. Med. Chem.*, 1996, 4:5-23.

Jin et al., "Novel analog of atrial natriuretic peptide selective for receptor-A produces increased diuresis and natriuresis in rats," *J. Clin. Invest.*, 1996, 98(4):969-976.

Köhler and milstein, "Continuous cultures of fused cells secreting antibody of predefined specificity," *Nature*, 1975, 256:495-497.

Kozbor and Roder, "The production of monoclonal antibodies from human lymphocytes," *Immunology Today*, 1983, 4(3):72-79.

Lewis, "PCR's competitors are alive and well and moving rapidly towards commercialization," *Genetic Engineering News*, 1992, 12(9):1.

Okolicany et al., "Clearance receptor and neutral endopeptidase-mediated metabolism of atrial natriuretic factor," *Am. J. Physiol, Renal. Physiol.*, 1992, 263:F546-F553.

Summerton and Weller, "Morpholino antisense oligomers: Design, preparation, and properties," *Antisense Nucleic Acid Drug Dev.*, 1997, 7:187-195.

Wei et al., "Atrial and pulmonary endothelin mRNA is increased in a canine model of chronic low cardiac output," *Am. J. Physiol.*, 1997, 273:R838-R844.

(Continued)

*Primary Examiner* — Elly-Gerald Stoica
(74) *Attorney, Agent, or Firm* — Fish & Richardson P.C.

(57) ABSTRACT

This document provides aquaretic and natriuretic polypeptides. For example, this document provides polypeptides having aquaretic and/or natriuretic activities. In some cases, a polypeptide provided herein can have aquaretic and natriuretic activities, while lacking the ability to lower blood pressure. This document also provides methods and materials for inducing aquaretic and/or natriuretic activities within a mammal.

14 Claims, 12 Drawing Sheets

(56) References Cited

OTHER PUBLICATIONS

Weiss, "Hot prospect for new gene amplifier," *Science*, 1991, 254(5036):1292-1293.
Wells, "Additivity of mutational effects in proteins," *Biochemistry*, 1990, 29(37):8509-8517.
Authorized Officer W. H. Shin, International Search Report and Written Opinion in International Application No. PCT/US2007/77900, mailed Feb. 19, 2008, 14 pages.
Authorized Officer D. Müllhausen, International Preliminary Report on Patentability in International Application No. PCT/US2007/77900, mailed Mar. 10, 2009, 6 pages.
Supplementary European Search Report in European Application No. 07842068, mailed Oct. 27, 2009, 5 pages.

```
R   M   D   R   I   G   L   S   K   G   C   F   G   L
AGG ATG GAC AGG ATT GGC TTG TCC AAG GGC TGC TTC GGC CTC

K   L   D   R   I   R   E   A   S   G   L   G   C   K
AAG CTG GAC CGA ATC AGG GAA GCG AGC GGC CTG GGA TGT AAA

V   L   R   R   H   (SEQ ID NO:4)
GTG CTG AGG CGG CAT (SEQ ID NO:5)
```

Figure 12

```
                         SEQUENCE LISTING

<160> NUMBER OF SEQ ID NOS: 8

<210> SEQ ID NO 1
<211> LENGTH: 5
<212> TYPE: PRT
<213> ORGANISM: Homo sapiens

<400> SEQUENCE: 1

Arg Met Asp Arg Ile
1               5

<210> SEQ ID NO 2
<211> LENGTH: 22
<212> TYPE: PRT
<213> ORGANISM: Artificial Sequence
<220> FEATURE:
<223> OTHER INFORMATION: amino acids 6-27 correspond to amino acids 1-22
      of human mature CNP with arginine, glutamic acid and alanine at
      positions 15, 16, and 17

<400> SEQUENCE: 2

Gly Leu Ser Lys Gly Cys Phe Gly Leu Lys Leu Asp Arg Ile Arg Glu
1               5                   10                  15

Ala Ser Gly Leu Gly Cys
            20

<210> SEQ ID NO 3
<211> LENGTH: 6
<212> TYPE: PRT
<213> ORGANISM: Homo sapiens

<400> SEQUENCE: 3

Lys Val Leu Arg Arg His
1               5

<210> SEQ ID NO 4
<211> LENGTH: 33
<212> TYPE: PRT
<213> ORGANISM: Artificial Sequence
<220> FEATURE:
<223> OTHER INFORMATION: combination of SEQ ID NOs:1, 2, and 3

<400> SEQUENCE: 4

Arg Met Asp Arg Ile Gly Leu Ser Lys Gly Cys Phe Gly Leu Lys Leu
1               5                   10                  15

Asp Arg Ile Arg Glu Ala Ser Gly Leu Gly Cys Lys Val Leu Arg Arg
            20                  25                  30

His

<210> SEQ ID NO 5
<211> LENGTH: 99
<212> TYPE: DNA
<213> ORGANISM: Artificial Sequence
<220> FEATURE:
<223> OTHER INFORMATION: nucleic acid encoding SEQ ID NO:4

<400> SEQUENCE: 5
aggatggaca ggattggctt gtccaagggc tgcttcggcc tcaagctgga ccgaatcagg      60
```

```
gaagcgagcg gcctgggatg taaagtgctg aggcggcat                              99
```

<210> SEQ ID NO 6
<211> LENGTH: 33
<212> TYPE: PRT
<213> ORGANISM: Artificial Sequence
<220> FEATURE:
<223> OTHER INFORMATION: combination of SEQ ID NOs:1, 7, and 3

<400> SEQUENCE: 6

Arg Met Asp Arg Ile Gly Leu Ser Lys Gly Cys Phe Gly Leu Lys Leu
1               5                   10                  15

Asp Arg Ile Gly Ser Met Ser Gly Leu Gly Cys Lys Val Leu Arg Arg
            20                  25                  30

His

<210> SEQ ID NO 7
<211> LENGTH: 22
<212> TYPE: PRT
<213> ORGANISM: Homo sapiens

<400> SEQUENCE: 7

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 8
<211> LENGTH: 28
<212> TYPE: PRT
<213> ORGANISM: Artificial Sequence
<220> FEATURE:
<223> OTHER INFORMATION: combination of SEQ ID NOs:2 and 3

<400> SEQUENCE: 8

Gly Leu Ser Lys Gly Cys Phe Gly Leu Lys Leu Asp Arg Ile Arg Glu
1               5                   10                  15

Ala Ser Gly Leu Gly Cys Lys Val Leu Arg Arg His
            20                  25

CHIMERIC AQUARETIC AND NATRIURETIC POLYPEPTIDES LACKING VASODILATORY ACTIVITY

CROSS-REFERENCE TO RELATED APPLICATIONS

This application is a divisional of U.S. application Ser. No. 12/440,053, filed Apr. 12, 2010, now U.S. Pat. No. 8,283,318, which is a National Stage application under 35 U.S.C. §371 of International Application No. PCT/US2007/077900, having an international filing date of Sep. 7, 2007, which claims benefit of U.S. Provisional Application No. 60/825,028, filed Sep. 8, 2006.

BACKGROUND

1. Technical Field

This document relates to aquaretic and natriuretic polypeptides. For example, this document relates to polypeptides having aquaretic and natriuretic activities while lacking the ability dilate vascular tissue.

2. Background Information

Members of the natriuretic polypeptide family are hormones that regulate body fluid homeostasis. Atrial natriuretic peptide (ANP) is secreted by atrial myocytes in response to increased intravascular volume. Once ANP is in the circulation, its effects are primarily on the kidney, vascular tissue, and adrenal gland, in which its actions lead to the excretion of sodium and water by the kidneys and a decrease in intravascular volume and blood pressure. BNP also is of myocardial cell origin, and like ANP, it circulates in human plasma. BNP is natriuretic, rennin inhibiting, vasodilating, and lusitropic. The main circulating and storage form of BNP is a 32 amino acid polypeptide with a ring structure. Physiological actions of BNP are mediated through a guanylate cyclase-linked receptor, natriuretic peptide receptor A (NPR-A). Clearance of BNP is promoted by a NPR-C receptor that removes it from the circulation. BNP also is degraded through enzymatic cleavage by neutral endopeptidase. C-type natriuretic peptide (CNP) is of endothelial cell origin and functions as a vasodilating and growth-inhibiting polypeptide. *Dendroaspis* natriuretic peptide (DNP) is similar in structure to ANP, BNP, and CNP, and is isolated from the venom of *Dendroaspis angusticeps* or green mamba snake.

SUMMARY

This document relates to aquaretic and natriuretic polypeptides. For example, this document provides polypeptides having aquaretic and natriuretic activities. In some cases, a polypeptide provided herein can have aquaretic and natriuretic activities, while lacking the ability to dilate vascular tissue.

In general, one aspect of this document features a polypeptide less than 45 amino acid residues in length, wherein the polypeptide comprises, or consists essentially of, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:2 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can be a substantially pure polypeptide.

In another embodiment, this document features an isolated nucleic acid encoding a polypeptide less than 45 amino acid residues in length, wherein the polypeptide comprises, or consists essentially of, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:2 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can be a substantially pure polypeptide.

In another embodiment, this document features a vector comprising, or consisting essentially of, a nucleic acid encoding a polypeptide less than 45 amino acid residues in length, wherein the polypeptide comprises, or consists essentially of, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:2 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can be a substantially pure polypeptide.

In another embodiment, this document features a host cell comprising a nucleic acid encoding a polypeptide less than 45 amino acid residues in length, wherein the polypeptide comprises, or consists essentially of, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:2 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can be a substantially pure polypeptide. The host cell can be a eukaryotic host cell.

In another embodiment, this document features a pharmaceutical composition comprising a pharmaceutically acceptable carrier and a polypeptide less than 45 amino acid residues in length, wherein the polypeptide comprises, or consists essentially of, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:2 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can be a substantially pure polypeptide.

In another embodiment, this document features a method for increasing aquaretic and natriuretic activity within a mammal without lowering blood pressure, wherein the method comprises administering, to the mammal, a polypeptide less than 45 amino acid residues in length, wherein the polypeptide comprises, or consists essentially of, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:2 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can be a substantially pure polypeptide.

In another embodiment, this document features a stent comprising a coating comprising a polypeptide less than 45 amino acid residues in length, wherein the polypeptide comprises, or consists essentially of, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:2 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can be a substantially pure polypeptide.

In another embodiment, this document features a dialysis tubing comprising a coating comprising a polypeptide less than 45 amino acid residues in length, wherein the polypeptide comprises, or consists essentially of, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:2 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can be a substantially pure polypeptide.

In another embodiment, this document features microparticles or nanoparticles comprising a polypeptide less than 45 amino acid residues in length, wherein the polypeptide comprises, or consists essentially of, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:2 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can be a substantially pure polypeptide.

In another embodiment, this document features a polypeptide less than 45 amino acid residues in length, wherein the polypeptide comprises, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:7 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can comprise the sequence set forth in SEQ ID NO:1. The polypeptide can comprise the sequence set forth in SEQ ID NO:7. The polypeptide can comprise the sequence set forth in SEQ ID NO:3. The polypeptide can comprise the sequence set forth in SEQ ID NO:1, the sequence set forth in SEQ ID NO:7, and the sequence set forth in SEQ ID NO:3. The polypeptide can be a substantially pure polypeptide.

In another embodiment, this document features an isolated nucleic acid encoding a polypeptide less than 45 amino acid residues in length, wherein the polypeptide comprises, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:7 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can comprise the sequence set forth in SEQ ID NO:1. The polypeptide can comprise the sequence set forth in SEQ ID NO:7. The polypeptide can comprise the sequence set forth in SEQ ID NO:3. The polypeptide can comprise the sequence set forth in SEQ ID NO:1, the sequence set forth in SEQ ID NO:7, and the sequence set forth in SEQ ID NO:3. The polypeptide can be a substantially pure polypeptide.

In another embodiment, this document features a vector comprising, or consisting essentially of, a nucleic acid encoding a polypeptide less than 45 amino acid residues in length, wherein the polypeptide comprises, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:7 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can comprise the sequence set forth in SEQ ID NO:1. The polypeptide can comprise the sequence set forth in SEQ ID NO:7. The polypeptide can comprise the sequence set forth in SEQ ID NO:3. The polypeptide can comprise the sequence set forth in SEQ ID NO:1, the sequence set forth in SEQ ID NO:7, and the sequence set forth in SEQ ID NO:3. The polypeptide can be a substantially pure polypeptide.

In another embodiment, this document features a host cell comprising a nucleic acid encoding a polypeptide less than 45 amino acid residues in length, wherein the polypeptide comprises, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:7 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can comprise the sequence set forth in SEQ ID NO:1. The polypeptide can comprise the sequence set forth in SEQ ID NO:7. The polypeptide can comprise the sequence set forth in SEQ ID NO:3. The polypeptide can comprise the sequence set forth in SEQ ID NO:1, the sequence set forth in SEQ ID NO:7, and the sequence set forth in SEQ ID NO:3. The polypeptide can be a substantially pure polypeptide.

In another embodiment, this document features a pharmaceutical composition comprising a pharmaceutically acceptable carrier and a polypeptide less than 45 amino acid residues in length, wherein the polypeptide comprises, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:7 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can comprise the sequence set forth in SEQ ID NO:1. The polypeptide can comprise the sequence set forth in SEQ ID NO:7. The polypeptide can comprise the sequence set forth in SEQ ID NO:3. The polypeptide can comprise the sequence set forth in SEQ ID NO:1, the sequence set forth in SEQ ID NO:7, and the sequence set forth in SEQ ID NO:3. The polypeptide can be a substantially pure polypeptide.

In another embodiment, this document features a stent comprising a coating comprising a polypeptide less than 45 amino acid residues in length, wherein the polypeptide comprises, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:7 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can comprise the sequence set forth in SEQ ID NO:1. The polypeptide can comprise the sequence set forth in SEQ ID NO:7. The polypeptide can comprise the sequence set forth in SEQ ID NO:3. The polypeptide can comprise the sequence set forth in SEQ ID NO:1, the sequence set forth in SEQ ID NO:7, and the sequence set forth in SEQ ID NO:3. The polypeptide can be a substantially pure polypeptide.

In another embodiment, this document features a dialysis tubing comprising a coating comprising a polypeptide less than 45 amino acid residues in length, wherein the polypeptide comprises, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:7 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can comprise the sequence set forth in SEQ ID NO:1. The polypeptide can comprise the sequence set forth in SEQ ID NO:7. The polypeptide can comprise the sequence set forth in SEQ ID NO:3. The polypeptide can comprise the sequence set forth in SEQ ID NO:1, the sequence set forth in SEQ ID NO:7, and the sequence set forth in SEQ ID NO:3. The polypeptide can be a substantially pure polypeptide.

In another embodiment, this document features microparticles or nanoparticles comprising a polypeptide less than 45 amino acid residues in length, wherein the polypeptide comprises, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:7 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can comprise the sequence set forth in SEQ ID NO:1. The polypeptide can comprise the sequence set forth in SEQ ID NO:7. The polypeptide can comprise the sequence set forth in SEQ ID NO:3. The polypeptide can comprise the sequence set forth in SEQ ID NO:1, the sequence set forth in SEQ ID NO:7, and the sequence set forth in SEQ ID NO:3. The polypeptide can be a substantially pure polypeptide.

In another embodiment, this document features a polypeptide less than 45 amino acid residues in length, wherein the polypeptide comprises, in an order from amino terminus to carboxy terminus: (a) the sequence set forth in SEQ ID NO:2 or the sequence set forth in SEQ ID NO:2 with no more than eight mismatches, and (b) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can lack the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:2 and the sequence set forth in SEQ ID NO:3. The polypeptide can be a substantially pure polypeptide.

In another embodiment, this document features an isolated nucleic acid encoding a polypeptide less than 45 amino acid residues in length, wherein the polypeptide comprises, in an order from amino terminus to carboxy terminus: (a) the sequence set forth in SEQ ID NO:2 or the sequence set forth in SEQ ID NO:2 with no more than eight mismatches, and (b) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can lack the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:2 and the sequence set forth in SEQ ID NO:3. The polypeptide can be a substantially pure polypeptide.

In another embodiment, this document features a vector comprising, or consisting essentially of, a nucleic acid encoding a polypeptide less than 45 amino acid residues in length, wherein the polypeptide comprises, in an order from amino terminus to carboxy terminus: (a) the sequence set forth in SEQ ID NO:2 or the sequence set forth in SEQ ID NO:2 with no more than eight mismatches, and (b) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can lack the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:2 and the sequence set forth in SEQ ID NO:3. The polypeptide can be a substantially pure polypeptide.

In another embodiment, this document features a host cell comprising a nucleic acid encoding a polypeptide less than 45 amino acid residues in length, wherein the polypeptide comprises, in an order from amino terminus to carboxy terminus: (a) the sequence set forth in SEQ ID NO:2 or the sequence set forth in SEQ ID NO:2 with no more than eight mismatches, and (b) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can lack the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:2 and the sequence set forth in SEQ ID NO:3. The polypeptide can be a substantially pure polypeptide.

In another embodiment, this document features a pharmaceutical composition comprising a pharmaceutically acceptable carrier and a polypeptide less than 45 amino acid residues in length, wherein the polypeptide comprises, in an order from amino terminus to carboxy terminus: (a) the sequence set forth in SEQ ID NO:2 or the sequence set forth in SEQ ID NO:2 with no more than eight mismatches, and (b) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can lack the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:2 and the sequence set forth in SEQ ID NO:3. The polypeptide can be a substantially pure polypeptide.

In another embodiment, this document features a method for increasing aquaretic and natriuretic activity within a mammal without lowering blood pressure, wherein the method comprises administering, to the mammal, a polypeptide less than 45 amino acid residues in length, wherein the polypeptide comprises, in an order from amino terminus to carboxy terminus: (a) the sequence set forth in SEQ ID NO:2 or the sequence set forth in SEQ ID NO:2 with no more than eight mismatches, and (b) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can lack the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:2 and the sequence set forth in SEQ ID NO:3. The polypeptide can be a substantially pure polypeptide.

In another embodiment, this document features a method for increasing aquaretic and natriuretic activity within a mammal without lowering blood pressure, wherein the method comprises administering, to the mammal, a polypeptide less than 45 amino acid residues in length, wherein the polypeptide comprises, in an order from amino terminus to carboxy terminus: (a) the sequence set forth in SEQ ID NO:2 or the sequence set forth in SEQ ID NO:2 with no more than eight mismatches, and (b) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can lack the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:2 and the sequence set forth in SEQ ID NO:3. The polypeptide can be a substantially pure polypeptide.

In another embodiment, this document features a stent comprising a coating comprising a polypeptide less than 45 amino acid residues in length, wherein the polypeptide comprises, in an order from amino terminus to carboxy terminus: (a) the sequence set forth in SEQ ID NO:2 or the sequence set forth in SEQ ID NO:2 with no more than eight mismatches, and (b) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can lack the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:2 and the sequence set forth in SEQ ID NO:3. The polypeptide can be a substantially pure polypeptide.

In another embodiment, this document features a dialysis tubing comprising a coating comprising a polypeptide less than 45 amino acid residues in length, wherein the polypeptide comprises, in an order from amino terminus to carboxy terminus: (a) the sequence set forth in SEQ ID NO:2 or the sequence set forth in SEQ ID NO:2 with no more than eight mismatches, and (b) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can lack the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:2 and the sequence set forth in SEQ ID NO:3. The polypeptide can be a substantially pure polypeptide.

In another embodiment, this document features microparticles or nanoparticles comprising a polypeptide less than 45 amino acid residues in length, wherein the polypeptide comprises, in an order from amino terminus to carboxy terminus: (a) the sequence set forth in SEQ ID NO:2 or the sequence set forth in SEQ ID NO:2 with no more than eight mismatches, and (b) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can lack the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:2 and the sequence set forth in SEQ ID NO:3. The polypeptide can be a substantially pure polypeptide.

In another embodiment, this document features method for treating a mammal having a cardiovascular or renal condition. The method can comprise administering a polypeptide to the mammal. The mammal can have cardiovascular disease. The mammal can have congestive heart failure. The mammal can have myocardial infarction, a coronary disease, an artery disease, a renal insufficiency, cancer, or a sodium and water retaining state.

In some cases, the polypeptide can be less than 45 amino acid residues in length, wherein the polypeptide comprises, or consists essentially of, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:2 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can be a substantially pure polypeptide.

In some cases, the polypeptide can be less than 45 amino acid residues in length, wherein the polypeptide comprises, in an order from amino terminus to carboxy terminus: (a) the sequence set forth in SEQ ID NO:1 or the sequence set forth in SEQ ID NO:1 with no more than three mismatches, (b) the sequence set forth in SEQ ID NO:7 or the sequence set forth in SEQ ID NO:2 with no more than eight mismatches, and (c) the sequence set forth in SEQ ID NO:3 or the sequence set forth in SEQ ID NO:3 with no more than three mismatches. The polypeptide can comprise natriuretic activity. The polypeptide can comprise the sequence set forth in SEQ ID NO:1. The polypeptide can comprise the sequence set forth in SEQ ID NO:7. The polypeptide can comprise the sequence set forth in SEQ ID NO:3. The polypeptide can comprise the sequence set forth in SEQ ID NO:1, the sequence set forth in SEQ ID NO:7, and the sequence set forth in SEQ ID NO:3. The polypeptide can be a substantially pure polypeptide.

In some cases, the polypeptide can be less than 45 amino acid residues in length, wherein the polypeptide comprises, in an order from amino terminus to carboxy terminus: (a) the sequence set forth in SEQ ID NO:2 or the sequence set forth in SEQ ID NO:2 with no more than eight mismatches, and (b) the sequence set forth in SEQ ID NO:3 or the sequence set forth in SEQ ID NO:3 with no more than three mismatches. The polypeptide can comprise natriuretic activity. The polypeptide can lack vasodilatory activity. The polypeptide can lack the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:2 and the sequence set forth in SEQ ID NO:3. The polypeptide can be a substantially pure polypeptide.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 12 contains a nucleic acid sequence (SEQ ID NO:5) that can encode an ABC-NP polypeptide having the amino acid sequence set forth in SEQ ID NO:4.

DETAILED DESCRIPTION

Figure 1:
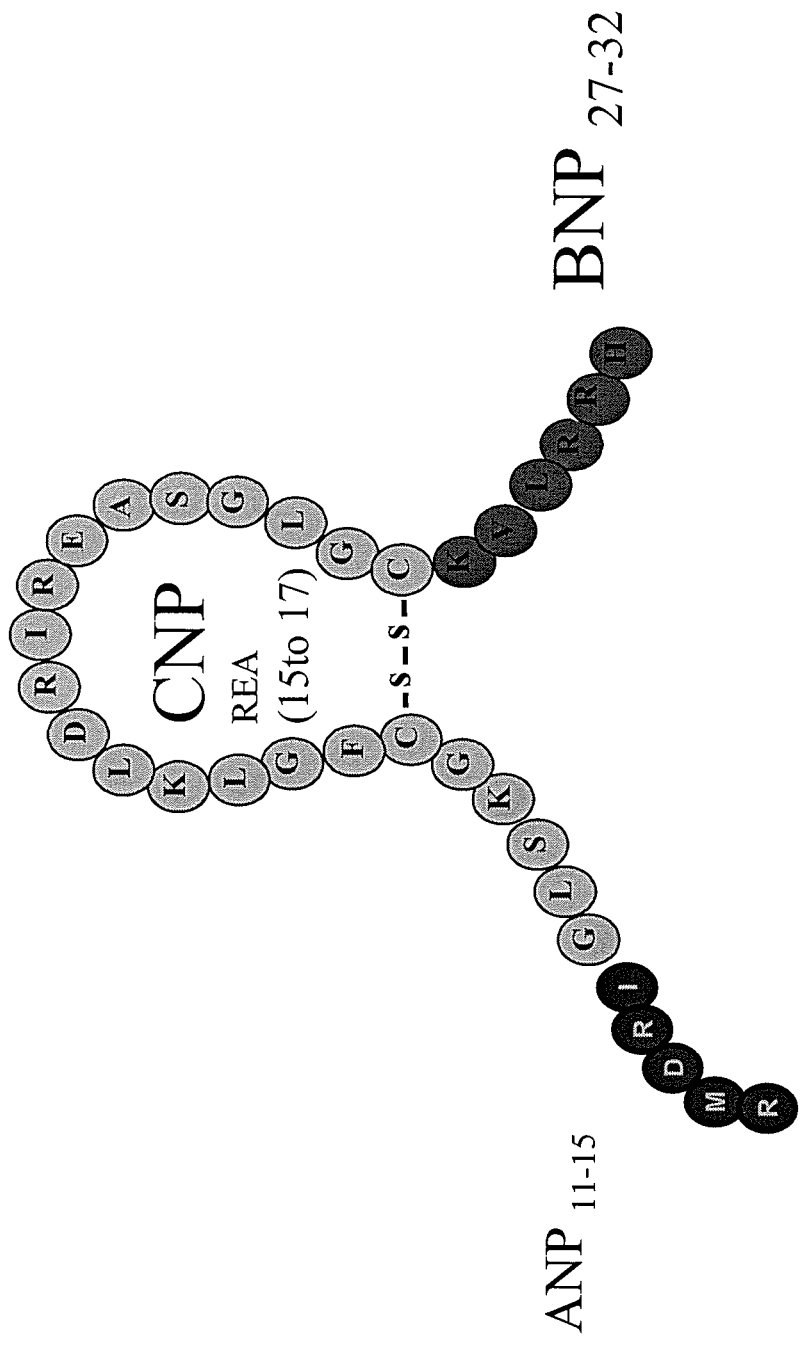
FIG. 1 is a schematic diagram of an ABC-NP polypeptide that is 33 amino acid residues in length (SEQ ID NO:4). The first five amino acid residues of SEQ ID NO:4 correspond to amino acid residues 11 to 15 of human mature ANP and are designated as SEQ ID NO:1. Amino acid residues 6 to 27 of SEQ ID NO:4 correspond to amino acid residues 1 to 22 of human mature CNP with the exception that the amino acid residues at positions 15, 16, and 17 are changed to arginine, glutamic acid, and alanine. Amino acid residues 6 to 27 of SEQ ID NO:4 are designated as SEQ ID NO:2. Amino acid residues 28 to 33 of SEQ ID NO:4 correspond to amino acid residues 27 to 32 of human mature BNP and are designated as SEQ ID NO:3.

This document relates to aquaretic and natriuretic polypeptides. For example, this document provides polypeptides having aquaretic and/or natriuretic activities. In some cases, a polypeptide provided herein can have aquaretic and natriuretic activities, while lacking the ability to lower blood pressure. This document also provides methods and materials for inducing aquaretic and/or natriuretic activities within a mammal.

A polypeptide provided herein can have any sequence and can have any length. For example, a polypeptide provided herein can include the sequence set forth in SEQ ID NO:1, SEQ ID NO:2, and SEQ ID NO:3. In some cases, a polypeptide provided herein can contain an amino acid sequence that aligns to (a) the sequence set forth in SEQ ID NO:1 with four or less (e.g., three or less, two or less, one, or zero) amino acid additions, deletions, substitutions, or combinations thereof, (b) the sequence set forth in SEQ ID NO:2 with ten or less (e.g., nine or less, eight or less, seven or less, six or less, five or less, four or less, three or less, two or less, one, or zero) amino acid additions, deletions, substitutions, or combinations thereof and (c) the sequence set forth in SEQ ID NO:3 with five or less (e.g., four or less, three or less, two or less, one, or zero) amino acid additions, deletions, substitutions, or combinations thereof. For example, a polypeptide provided herein can contain the sequence set forth in SEQ ID NO:1 with the exception that the first arginine residue or the last isoleucine residue of SEQ ID NO:1 is deleted or replaced with a different amino acid residue.

In some cases, a polypeptide provided herein can contain (a) a first amino acid sequence that either is set forth in SEQ ID NO:1 or aligns to the sequence set forth in SEQ ID NO:1 with four or less (e.g., three or less, two or less, one, or zero) amino acid deletions, substitutions, or combinations thereof, (b) a second amino acid sequence that either is set forth in SEQ ID NO:2 or aligns to the sequence set forth in SEQ ID NO:2 with ten or less (e.g., nine or less, eight or less, seven or less, six or less, five or less, four or less, three or less, two or less, one, or zero) amino acid additions, substitutions, or combinations thereof, and (a) a third amino acid sequence that either is set forth in SEQ ID NO:3 or aligns to the sequence set forth in SEQ ID NO:3 with five or less (e.g., four or less, three or less, two or less, one, or zero) amino acid deletions, substitutions, or combinations thereof. For example, a polypeptide provided herein can comprise or consist of the sequence set forth in SEQ ID NO:4.

In some cases, a polypeptide provided herein can include the sequence set forth in SEQ ID NO:1, SEQ ID NO:7, and SEQ ID NO:3. In some cases, a polypeptide provided herein can contain an amino acid sequence that aligns to (a) the sequence set forth in SEQ ID NO:1 with four or less (e.g., three or less, two or less, one, or zero) amino acid additions, deletions, substitutions, or combinations thereof, (b) the sequence set forth in SEQ ID NO:7 with ten or less (e.g., nine or less, eight or less, seven or less, six or less, five or less, four or less, three or less, two or less, one, or zero) amino acid additions, deletions, substitutions, or combinations thereof and (c) the sequence set forth in SEQ ID NO:3 with five or less (e.g., four or less, three or less, two or less, one, or zero) amino acid additions, deletions, substitutions, or combinations thereof. For example, a polypeptide provided herein can contain the sequence set forth in SEQ ID NO:1 with the exception that the first arginine residue or the last isoleucine residue of SEQ ID NO:1 is deleted or replaced with a different amino acid residue.

In some cases, a polypeptide provided herein can contain (a) a first amino acid sequence that either is set forth in SEQ ID NO:1 or aligns to the sequence set forth in SEQ ID NO:1 with four or less (e.g., three or less, two or less, one, or zero) amino acid deletions, substitutions, or combinations thereof, (b) a second amino acid sequence that either is set forth in SEQ ID NO:7 or aligns to the sequence set forth in SEQ ID NO:7 with ten or less (e.g., nine or less, eight or less, seven or less, six or less, five or less, four or less, three or less, two or less, one, or zero) amino acid additions, substitutions, or combinations thereof, and (a) a third amino acid sequence that either is set forth in SEQ ID NO:3 or aligns to the sequence set forth in SEQ ID NO:3 with five or less (e.g., four or less, three or less, two or less, one, or zero) amino acid deletions, substitutions, or combinations thereof. For example, a polypeptide provided herein can comprise or consist of the sequence set forth in SEQ ID NO:6.

In some cases, a polypeptide provided herein can include the sequence set forth in SEQ ID NO:2 and SEQ ID NO:3. In some cases, a polypeptide provided herein can contain an amino acid sequence that aligns to (a) the sequence set forth in SEQ ID NO:2 with ten or less (e.g., nine or less, eight or less, seven or less, six or less, five or less, four or less, three or less, two or less, one, or zero) amino acid additions, deletions, substitutions, or combinations thereof and (b) the sequence set forth in SEQ ID NO:3 with five or less (e.g., four or less, three or less, two or less, one, or zero) amino acid additions, deletions, substitutions, or combinations thereof. For example, a polypeptide provided herein can contain the sequence set forth in SEQ ID NO:2 with the exception that the first glycine residue of SEQ ID NO:2 is deleted or replaced with a different amino acid residue.

In some cases, a polypeptide provided herein can contain (a) a first amino acid sequence that either is set forth in SEQ ID NO:2 or aligns to the sequence set forth in SEQ ID NO:2 with ten or less (e.g., nine or less, eight or less, seven or less, six or less, five or less, four or less, three or less, two or less, one, or zero) amino acid additions, substitutions, or combinations thereof and (b) a second amino acid sequence that either is set forth in SEQ ID NO:3 or aligns to the sequence set forth in SEQ ID NO:3 with five or less (e.g., four or less, three or less, two or less, one, or zero) amino acid deletions, substitutions, or combinations thereof. For example, a polypeptide provided herein can comprise or consist of the sequence set forth in SEQ ID NO:8.

A polypeptide provided herein can have any length. For example, a polypeptide provided herein can be between 25 and 45 (e.g., between 26 and 44, between 27 and 43, between 28 and 42, between 29 and 41, between 30 and 40, between 31 and 39, or between 32 and 38) amino acid residues in length. It will be appreciated that a polypeptide with a length of 25 or 45 amino acid residues is a polypeptide with a length between 25 and 45 amino acid residues.

In some cases, a polypeptide provided herein can be a substantially pure polypeptide. As used herein, the term "substantially pure" with reference to a polypeptide means that the polypeptide is substantially free of other polypeptides, lipids, carbohydrates, and nucleic acid with which it is naturally associated. Thus, a substantially pure polypeptide is any polypeptide that is removed from its natural environment and is at least 60 percent pure or is any chemically synthesized polypeptide. A substantially pure polypeptide can be at least about 60, 65, 70, 75, 80, 85, 90, 95, or 99 percent pure. Typically, a substantially pure polypeptide will yield a single major band on a non-reducing polyacrylamide gel.

In some embodiments, a polypeptide provided herein can lack vasoactivity. Vasoactivity can be assessed by determining responsivity of a blood vessel (e.g., a carotid artery in an organ chamber) to the polypeptide.

A polypeptide provide herein can be obtained by expression of a recombinant nucleic acid encoding the polypeptide or by chemical synthesis. For example, standard recombinant technology using expression vectors encoding a polypeptide provide herein can be used. The resulting polypeptides then can be purified using, for example, affinity chromatographic techniques and HPLC. The extent of purification can be measured by any appropriate method, including but not limited to: column chromatography, polyacrylamide gel electrophoresis, or high-performance liquid chromatography. A polypeptide provide herein can be designed or engineered to contain a tag sequence that allows the polypeptide to be purified (e.g., captured onto an affinity matrix). For example, a tag such as c-myc, hemagglutinin, polyhistidine, or Flag™ tag (Kodak) can be used to aid polypeptide purification. Such tags can be inserted anywhere within the polypeptide including at either the carboxyl or amino termini. Other fusions that can be used include enzymes that aid in the detection of the polypeptide, such as alkaline phosphatase.

A polypeptide provided herein can be produced to contain three regions, a first region that includes an N-terminus (e.g., an N-terminus sequence from an ANP polypeptide), a second region that includes a ring structure of a mature natriuretic polypeptide such as a CNP polypeptide, and a third region that includes a C-terminus (e.g., a C-terminus sequence from a BNP polypeptide). The N-termini, ring structures, and C-termini of BNP, DNP, ANP, and CNP are described elsewhere. See, e.g., U.S. patent application Ser. No. 10/561,014.

A polypeptide provided herein can be used to treat cardiovascular diseases, congestive heart failure, myocardial infarction, coronary artery diseases, renal diseases, anti-ischemic renal diseases, anti-inflammatory renal diseases, anti-fibrotic renal diseases, hepatic diseases, cancer (e.g., adenocarcinoma, squamous cell cancer, small cell lung cancer, or breast cancer), pulmonary hypertension, vascular diseases, diastolic dysfunction, cardiac dysfunction, renal insufficiency (e.g., contrast induced or ischemic induced renal insufficiency) or combinations thereof. For example, an ABC-NP polypeptide can be administered to a human having coronary artery disease under conditions wherein the severity of the human's coronary artery disease symptoms is reduced.

A polypeptide provided herein can be formulated as a pharmaceutical composition by admixture with pharmaceutically acceptable non-toxic excipients or carriers. Such compositions can be administered to a subject in need thereof in an amount effective to treat, for example, heart, liver, vascular, kidney, or other sodium retaining conditions. Pharmaceutical compositions may be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Compositions for other routes of administration may be prepared as desired using standard methods.

Formulations for parenteral administration may contain as common excipients sterile water or saline, polyalkylene glycols such as polyethylene glycol, oils of vegetable origin, hydrogenated naphthalenes, and the like. In particular, biocompatible, biodegradable lactide polymer, lactide/glycolide copolymer, or polyoxethylene-polyoxypropylene copolymers are examples of excipients for controlling the release of the polypeptide in vivo. Other suitable parenteral delivery systems include ethylene-vinyl acetate copolymer particles, osmotic pumps, implantable infusion systems, and liposomes. Formulations for inhalation administration may contain excipients such as lactose, if desired. Inhalation formulations may be aqueous solutions containing, for example, polyoxyethylene-9-lauryl ether, glycocholate and deoxycholate, or they may be oily solutions for administration in the form of nasal drops. If desired, the compounds can be formulated as gels to be applied intranasally. Formulations for parenteral administration may also include glycocholate for buccal administration For oral administration, tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulfate). Tablets can be coated by methods known in the art. Preparations for oral administration can also be formulated to give controlled release of the compound.

Nasal preparations can be presented in a liquid form or as a dry product. Nebulized aqueous suspensions or solutions can include carriers or excipients to adjust pH and/or tonicity.

In some cases, a polypeptide provided herein can be formulated as a sustained release dosage form. For example, an ABC-NP, ABC-NP1, or BC-NP2 polypeptide can be formulated into a controlled release formulation. In some cases, coatings, envelopes, or protective matrices can be formulated to contain one or more of the polypeptides provided herein. Such coatings, envelopes, and protective matrices can be used to coat indwelling devices such as stents, catheters, and peritoneal dialysis tubing. In some cases, a polypeptide provided herein can be incorporated into a polymeric substances, liposomes, microemulsions, microparticles, nanoparticles, or waxes.

Nucleic Acids Encoding Polypeptides

This document also provides isolated nucleic acids that encode one or more of the polypeptides provided herein. The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid (e.g., a nucleic acid encoding a polypeptide comprising or consisting of the amino acid sequence set forth in SEQ ID NO:4, 6, or 8) can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence. A nucleic acid existing among hundreds to millions of other nucleic acids within, for example, cDNA libraries or genomic libraries, or gel slices containing a genomic DNA restriction digest, is not to be considered an isolated nucleic acid.

As used herein, the term "nucleic acid" refers to both RNA and DNA, including mRNA, cDNA, genomic DNA, synthetic (e.g., chemically synthesized) DNA, and nucleic acid analogs. The nucleic acid can be double-stranded or single-stranded, and where single-stranded, can be the sense strand or the antisense strand. In addition, nucleic acid can be circular or linear. Nucleic acid analogs can be modified at the base moiety, sugar moiety, or phosphate backbone to improve, for example, stability, hybridization, or solubility of a nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone and the four bases are retained. See, for example, Summerton and Weller *Antisense Nucleic Acid Drug Dev.*, 7:187-195 (1997); and Hyrup et al. *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

A nucleic acid provided herein can comprise or consist of the sequence set forth in SEQ ID NO:5.

Typically, an isolated nucleic acid provided herein is at least 10 nucleotides in length (e.g., 10, 15, 20, 25, 30, 35, 40, 50, 75, 100, 200, 300, 350, 400, or more nucleotides in length). Nucleic acid molecules that are less than full-length can be useful, for example, as primers or probes for diagnostic purposes. Isolated nucleic acid molecules can be produced by standard techniques, including, without limitation, common molecular cloning and chemical nucleic acid synthesis techniques. For example, polymerase chain reaction (PCR) techniques can be used. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 15 to 50 nucleotides in length, but can range from 10 nucleotides to hundreds of nucleotides in length. For example, a primer can be 12, 15, 16, 17, 18, 19, 20, 21, 22, 23, 24, 25, 26, 27, 28, 29, 30, 35, 40, or 45 nucleotides in length. A primer can be purified from a restriction digest by conventional methods, or can be chemically synthesized. Primers typically are single-stranded for maximum efficiency in amplification, but a primer can be double-stranded. Double-stranded primers are first denatured (e.g., treated with heat) to separate the strands before use in amplification. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids as described elsewhere (Lewis, *Genetic Engineering News,* 12(9):1 (1992); Guatelli et al., *Proc. Natl. Acad. Sci. USA,* 87:1874-1878 (1990); and Weiss, *Science,* 254:1292 (1991)).

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids also can be obtained by mutagenesis. For example, a nucleic acid sequence encoding a polypeptide having the sequence set forth in SEQ ID NO:1, 2, 3, 4, 6, 7, or 8 can be mutated using standard techniques such as, for example, oligonucleotide-directed mutagenesis and/or site-directed mutagenesis through PCR. See, *Short Protocols in Molecular Biology*, Chapter 8, Green Publishing Associates and John Wiley & Sons, Edited by Ausubel et al., 1992. Such mutations include additions, deletions, substitutions, and combinations thereof.

Vectors and Host Cells

This document also provides vectors containing a nucleic acid provided herein. As used herein, a "vector" is a replicon, such as a plasmid, phage, or cosmid, into which another DNA segment may be inserted so as to bring about the replication of the inserted segment. A vector can be an expression vector. An "expression vector" is a vector that includes one or more expression control sequences, and an "expression control sequence" is a DNA sequence that controls and regulates the transcription and/or translation of another DNA sequence.

In an expression vector provided herein, the nucleic acid can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it can be necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the polypeptide encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, poxviruses, adenoviruses, and adeno-associated viruses. Numerous vectors and expression systems are commercially available from such corporations as Novagen (Madison, Wis.), Clonetech (Palo Alto, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

This document also provides host cells containing a nucleic acid molecule and/or nucleic acid vector provided herein. The term "host cell" is intended to include prokaryotic and eukaryotic cells into which a nucleic acid molecule or vector can be introduced. Any method can be used to introduce nucleic acid into a cell. For example, calcium phosphate precipitation, electroporation, heat shock, lipofection, microinjection, and viral-mediated nucleic acid transfer can be used introduce nucleic acid into cells. In addition, naked DNA can be delivered directly to cells in vivo as described elsewhere (U.S. Pat. Nos. 5,580,859 and 5,589,466).

Detecting Polypeptides

This document provides methods and materials for detecting a polypeptide provided herein. Such methods and materials can be used to monitor polypeptide levels within a mammal receiving the polypeptide as a therapeutic. A polypeptide provided herein (e.g., an ABC-NP, ABC-NP1, or BC-NP2 polypeptide) can be detected, for example, immunologically using one or more antibodies. As used herein, the term "antibody" includes intact molecules as well as fragments thereof that are capable of binding to an epitopic determinant of a polypeptide provided herein. The term "epitope" refers to an antigenic determinant on an antigen to which the paratope of an antibody binds. Epitopic determinants usually consist of chemically active surface groupings of molecules such as amino acids or sugar side chains, and typically have specific three-dimensional structural characteristics, as well as specific charge characteristics. Epitopes generally have at least five contiguous amino acids (a continuous epitope), or alternatively can be a set of noncontiguous amino acids that define a particular structure (e.g., a conformational epitope). The term "antibody" includes polyclonal antibodies, monoclonal antibodies, humanized or chimeric antibodies, single chain Fv antibody fragments, Fab fragments, and $F(ab)_2$ fragments. Polyclonal antibodies are heterogeneous populations of antibody molecules that are contained in the sera of the immunized animals. Monoclonal antibodies are homogeneous populations of antibodies to a particular epitope of an antigen.

Antibody fragments that have specific binding affinity for a polypeptide provided herein (e.g., ABC-NP, ABC-NP1, or BC-NP2) can be generated by known techniques. For example, F(ab')2 fragments can be produced by pepsin digestion of the antibody molecule; Fab fragments can be generated by reducing the disulfide bridges of F(ab')2 fragments. Alternatively, Fab expression libraries can be constructed. See, for example, Huse et al., *Science*, 246:1275 (1989). Once produced, antibodies or fragments thereof are tested for recognition of a polypeptide provided herein by standard immunoassay methods including ELISA techniques, radioimmunoassays, and Western blotting. See, *Short Protocols in Molecular Biology*, Chapter 11, Green Publishing Associates and John Wiley & Sons, Edited by Ausubel, F. M. et al., 1992.

In immunological assays, an antibody having specific binding affinity for a polypeptide provided herein or a secondary antibody that binds to such an antibody can be labeled, either directly or indirectly. Suitable labels include, without limitation, radionuclides (e.g., $^{125}I$, $^{131}I$, $^{35}S$, $^{3}H$, $^{32}P$, $^{33}P$ or $^{14}C$), fluorescent moieties (e.g., fluorescein, FITC, PerCP, rhodamine, or PE), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). Antibodies can be indirectly labeled by conjugation with biotin then detected with avidin or streptavidin labeled with a molecule described above. Methods of detecting or quantifying a label depend on the nature of the label and are known in the art. Examples of detectors include, without limitation, x-ray film, radioactivity counters, scintillation counters, spectrophotometers, colorimeters, fluorometers, luminometers, and densitometers. Combinations of these approaches (including "multi-layer" assays) familiar to those in the art can be used to enhance the sensitivity of assays.

Immunological assays for detecting a polypeptide provided herein can be performed in a variety of known formats, including sandwich assays, competition assays (competitive RIA), or bridge immunoassays. See, for example, U.S. Pat. Nos. 5,296,347; 4,233,402; 4,098,876; and 4,034,074. Methods of detecting a polypeptide provided herein generally include contacting a biological sample with an antibody that binds to a polypeptide provided herein and detecting binding of the polypeptide to the antibody. For example, an antibody having specific binding affinity for a polypeptide provided herein can be immobilized on a solid substrate by any of a variety of methods known in the art and then exposed to the biological sample. Binding of the polypeptide to the antibody on the solid substrate can be detected by exploiting the phenomenon of surface plasmon resonance, which results in a change in the intensity of surface plasmon resonance upon binding that can be detected qualitatively or quantitatively by an appropriate instrument, e.g., a Biacore apparatus (Biacore International AB, Rapsgatan, Sweden). Alternatively, the antibody is labeled and detected as described above. A standard curve using known quantities of a polypeptide provided herein can be generated to aid in the quantitation of the levels of the polypeptide.

In other embodiments, a "sandwich" assay in which a capture antibody is immobilized on a solid substrate is used to detect the presence, absence, or level of a polypeptide provided herein. The solid substrate can be contacted with the biological sample such that any polypeptide of interest in the sample can bind to the immobilized antibody. The presence, absence, or level of the polypeptide bound to the antibody can be determined using a "detection" antibody having specific binding affinity for the polypeptide. In some embodiments, a capture antibody can be used that has binding affinity for BNP as well as a polypeptide provided herein. In this embodiment, a detection antibody can be used that has specific binding affinity for a particular polypeptide provided herein. It is understood that in sandwich assays, the capture antibody should not bind to the same epitope (or range of epitopes in the case of a polyclonal antibody) as the detection antibody. Thus, if a monoclonal antibody is used as a capture antibody, the detection antibody can be another monoclonal antibody that binds to an epitope that is either completely physically separated from or only partially overlaps with the epitope to which the capture monoclonal antibody binds, or a polyclonal antibody that binds to epitopes other than or in addition to that to which the capture monoclonal antibody binds. If a polyclonal antibody is used as a capture antibody, the detection antibody can be either a monoclonal antibody that binds to an epitope that is either completely physically separated from or partially overlaps with any of the epitopes to which the capture polyclonal antibody binds, or a polyclonal antibody that binds to epitopes other than or in addition to that to which the capture polyclonal antibody binds. Sandwich assays can be performed as sandwich ELISA assays, sandwich Western blotting assays, or sandwich immunomagnetic detection assays.

Suitable solid substrates to which an antibody (e.g., a capture antibody) can be bound include, without limitation, microtiter plates, tubes, membranes such as nylon or nitrocellulose membranes, and beads or particles (e.g., agarose, cellulose, glass, polystyrene, polyacrylamide, magnetic, or magnetizable beads or particles). Magnetic or magnetizable particles can be particularly useful when an automated immunoassay system is used.

Antibodies having specific binding affinity for a polypeptide provided herein can be produced through standard methods. In general, a polypeptide can be recombinantly produced as described above, or can be purified from a biological sample (e.g., a heterologous expression system), and used to immunize host animals, including rabbits, chickens, mice, guinea pigs, or rats. For example, a polypeptide having the amino acid sequence set forth in SEQ ID NO:4, 6, or 8 (or fragments thereof that are at least six amino acids in length), can be used to immunize an animal. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Monoclonal antibodies can be prepared using a polypeptide provided herein and standard hybridoma technology. In particular, monoclonal antibodies can be obtained by any technique that provides for the production of antibody molecules by continuous cell lines in culture such as described by Kohler et al., *Nature*, 256:495 (1975), the human B-cell hybridoma technique (Kosbor et al., *Immunology Today*, 4:72 (1983); Cole et al., *Proc. Natl. Acad. Sci. USA*, 80:2026 (1983)), and the EBV-hybridoma technique (Cole et al., "Monoclonal Antibodies and Cancer Therapy," Alan R. Liss, Inc., pp. 77-96 (1983)). Such antibodies can be of any immunoglobulin class including IgG, IgM, IgE, IgA, IgD, and any subclass thereof. The hybridoma producing the monoclonal antibodies can be cultivated in vitro and in vivo.

Alternative techniques for detecting a polypeptide provided herein include mass-spectrophotometric techniques such as electrospray ionization (ESI), and matrix-assisted laser desorption-ionization (MALDI). See, for example, Gevaert et al., *Electrophoresis*, 22(9):1645-51 (2001); Chaurand et al., *J. Am. Soc. Mass Spectrom.*, 10(2):91-103 (1999). Mass spectrometers useful for such applications are available from Applied Biosystems (Foster City, Calif.); Bruker Daltronics (Billerica, Mass.); and Amersham Pharmacia (Sunnyvale, Calif.).

The invention will be further described in the following examples, which do not limit the scope of the invention described in the claims.

EXAMPLES

Example 1

Biological Effects of ABC-NP, ABC-NP 1, and BC-NP2 Polypeptides

Figure 2:
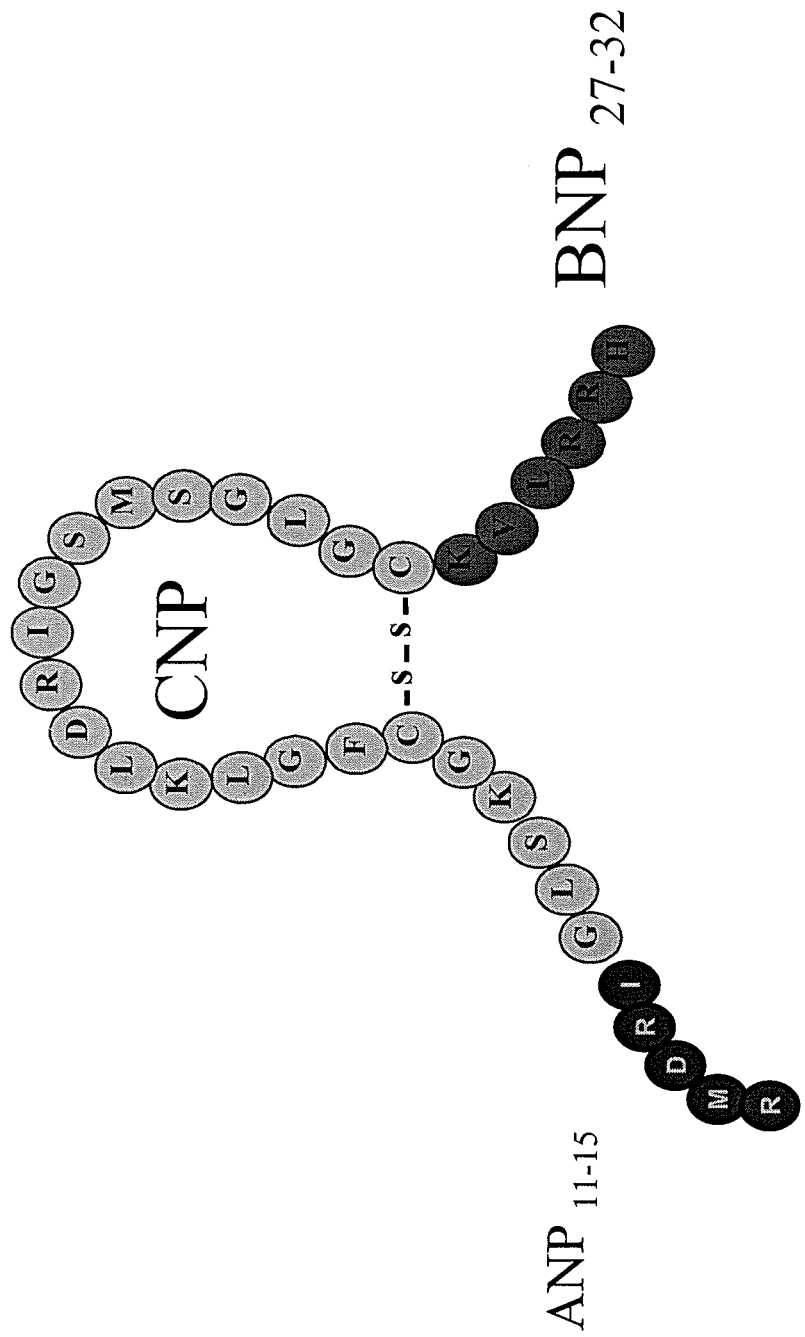
FIG. 2 is a schematic diagram of an ABC-NP1 polypeptide that is 33 amino acid residues in length (SEQ ID NO:6). The first five amino acid residues of SEQ ID NO:6 correspond to amino acid residues 11 to 15 of human mature ANP and are designated as SEQ ID NO:1. Amino acid residues 6 to 27 of SEQ ID NO:6 correspond to amino acid residues 1 to 22 of human mature CNP and are designated as SEQ ID NO:7. Amino acid residues 28 to 33 of SEQ ID NO:6 correspond to amino acid residues 27 to 32 of human mature BNP and are designated as SEQ ID NO:3.
Figure 3:
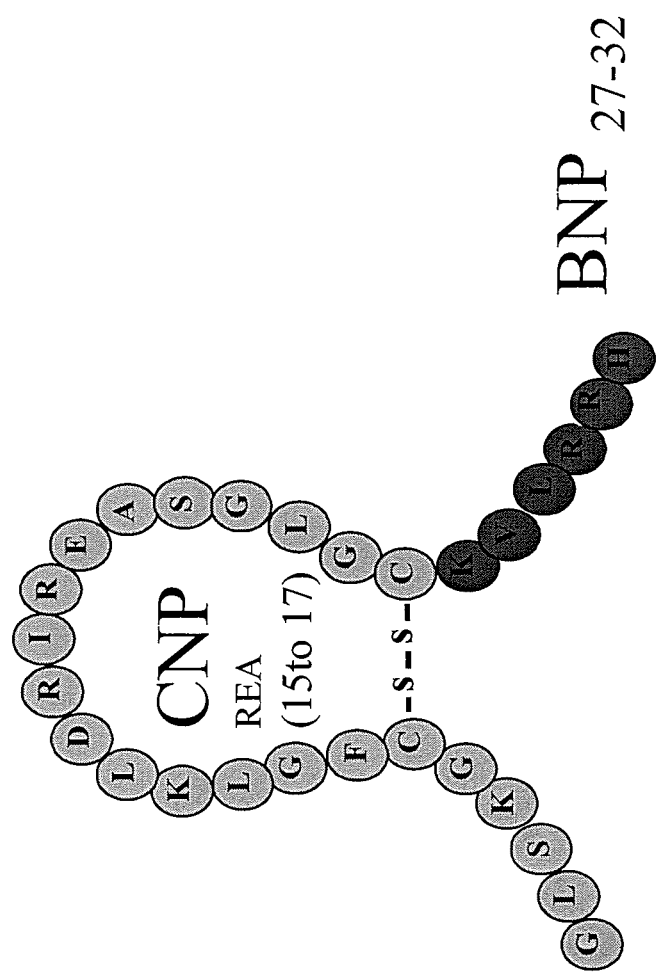
FIG. 3 is a schematic diagram of a BC-NP2 polypeptide that is 28 amino acid residues in length (SEQ ID NO:8). Amino acid residues 1 to 22 of SEQ ID NO:8 correspond to amino acid residues 1 to 22 of human mature CNP with the exception that the amino acid residues at positions 15, 16, and 17 are changed to arginine, glutamic acid, and alanine. Amino acid residues 1 to 22 of SEQ ID NO:8 are designated as SEQ ID NO:2. Amino acid residues 23 to 28 of SEQ ID NO:8 correspond to amino acid residues 27 to 32 of human mature BNP and are designated as SEQ ID NO:3.

Polypeptides with the sequences set forth in FIGS. 1-3 were designed and synthesized. The polypeptide set forth in FIG. 1 is referred to as an ABC-NP polypeptide; the polypeptide set forth in FIG. 2 is referred to as an ABC-NP1 polypeptide; and the polypeptide set forth in FIG. 3 is referred to as a BC-NP2 polypeptide. The biological effects of intravenous ABC-NP, ABC-NP1, or BC-NP2 infusion were tested in normal dogs. Briefly, five normal dogs were infused with 25 µg of ABC-NP, ABC-NP1, or BC-NP2 per kg administered as an IV bolus. Urinary sodium excretion, urine flow, mean arterial blood pressure, plasma vasopressin levels, and renal blood flow were measured as described elsewhere (Chen et al., *Am. J. Physiol. Regul. Integr. Comp. Physiol.*, 288: R1093-R1097 (2005) and Haber et al., *J. Clin. Endocrinol. Metab.*, 29:1349-1355 (2005)). The results were compared to results obtained from dogs treated with 25 μg of BNP per kg administered as an IV bolus.

Figure 4:
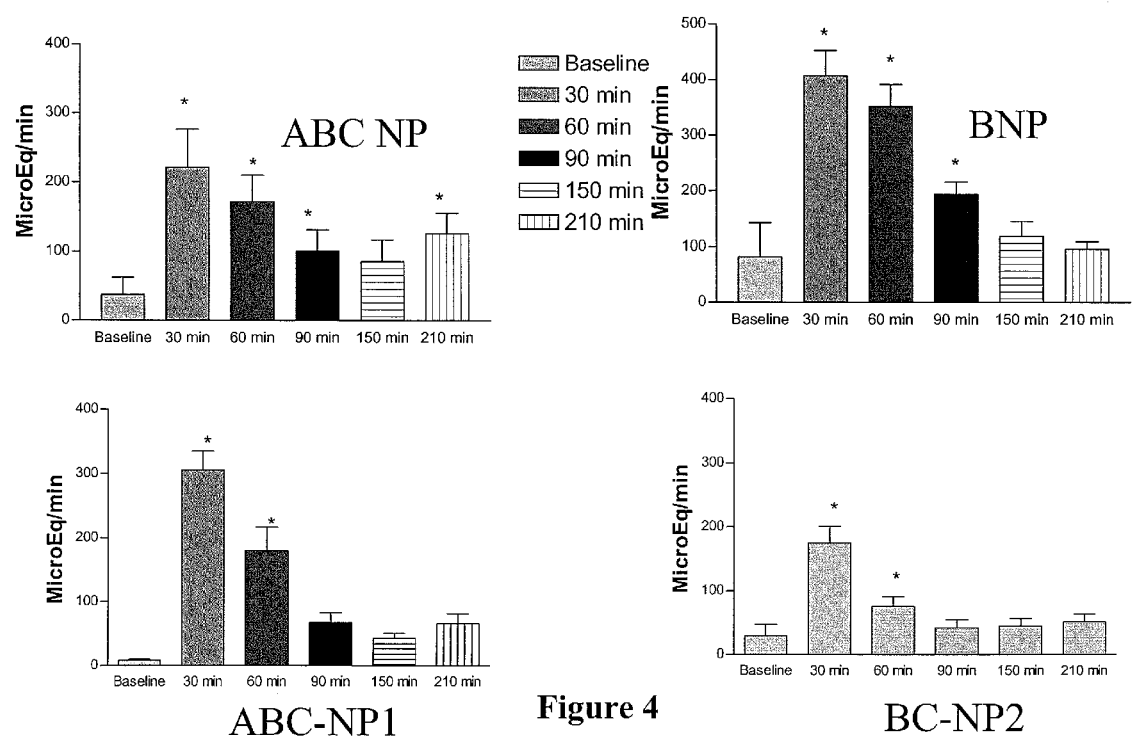
FIG. 4 contains four bar graphs plotting urinary sodium excretion rates for dogs treated with ABC-NP, BNP, ABC-NP, or BC-NP2 (25 mg per kg administered as an IV bolus). Baseline is prior to administration, whereas the indicated times are post administration.
Figure 5:
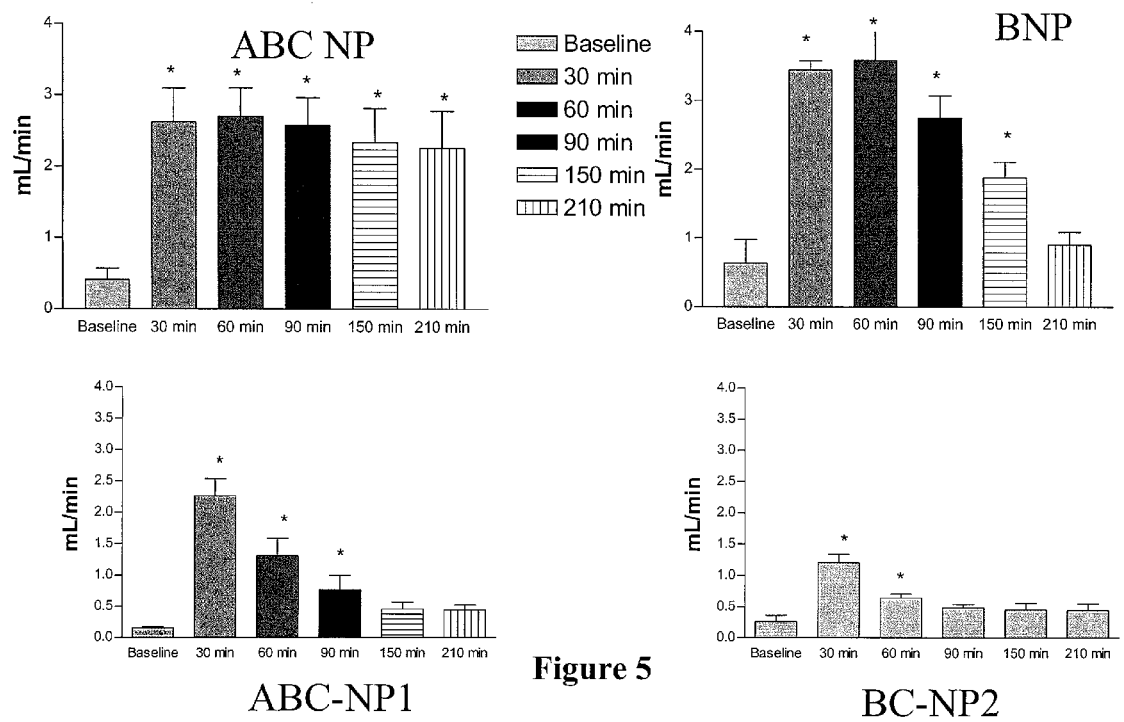
FIG. 5 contains four bar graphs plotting urine flow rates for dogs treated with ABC-NP, BNP, ABC-NP, or BC-NP2 (25 µg per kg administered as an IV bolus). Baseline is prior to administration, whereas the indicated times are post administration.
Figure 6:
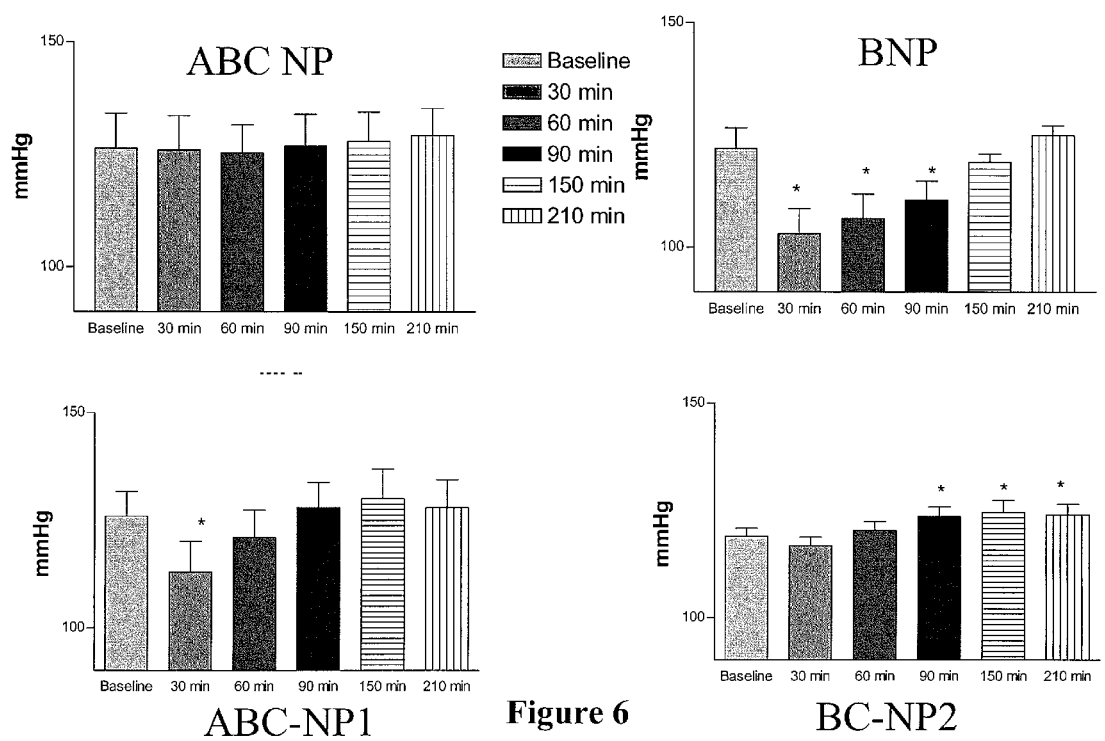
FIG. 6 contains four bar graphs plotting mean arterial blood pressure levels for dogs treated with ABC-NP, BNP, ABC-NP, or BC-NP2 (25 µg per kg administered as an IV bolus). Baseline is prior to administration, whereas the indicated times are post administration.
Figure 7:
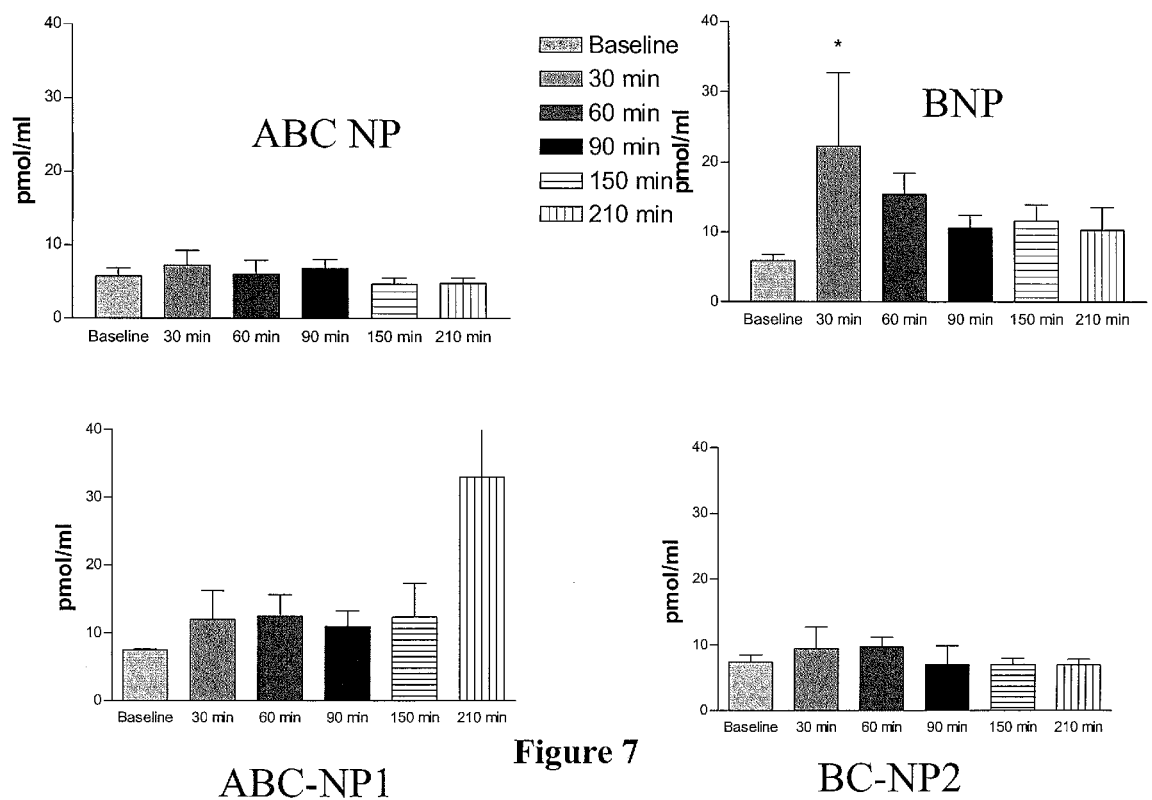
FIG. 7 contains four bar graphs plotting plasma vasopressin levels for dogs treated with ABC-NP, BNP, ABC-NP, or BC-NP2 (25 µg per kg administered as an IV bolus). Baseline is prior to administration, whereas the indicated times are post administration.

Systemic administration of the ABC-NP polypeptide resulted in aquaretic and natriuretic effects (FIGS. 4 and 5). Systemic administration of the ABC-NP polypeptide had no effect on mean arterial blood pressure (FIG. 6). Systemic administration of the ABC-NP polypeptide did not increase plasma vasopressin levels (FIG. 7). Plasma vasopressin levels increased following administration of BNP (FIG. 7). Both ABC-NP and BNP resulted in a similar decrease cardiac filling pressures.

These results demonstrate that the ABC-NP polypeptide has distinct renal effects and lacks the ability to affect systemic blood pressure as compared to BNP.

Figure 8:
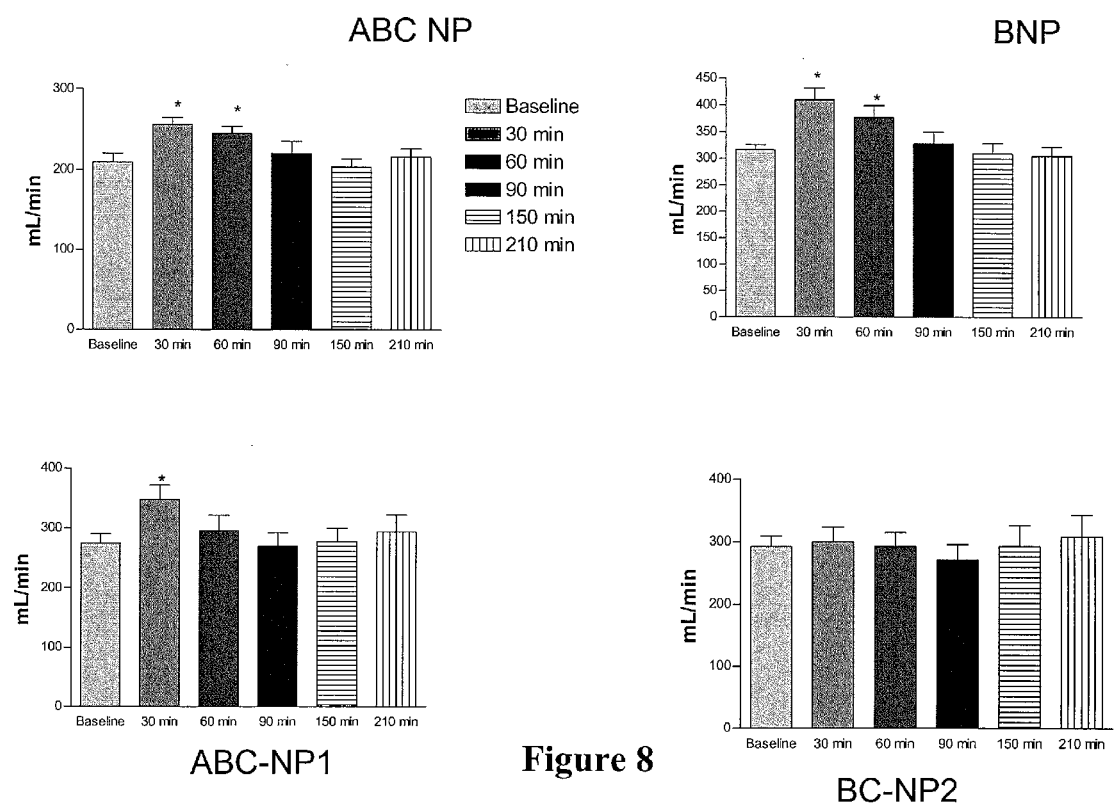
FIG. 8 contains four bar graphs plotting renal blood flow for dogs treated with ABC-NP, BNP, ABC-NP, or BC-NP2 (25 µg per kg administered as an IV bolus). Baseline is prior to administration, whereas the indicated times are post administration.

Treatment with ABC-NP1 caused a reduction in mean arterial blood pressure and an increase in renal blood flow (FIGS. 6 and 8). There was no prolonged aquaretic and diuretic renal actions observed in dogs treated with ABC-NP1, which were observed in dogs treated with ABC-NP (FIGS. 4 and 5). Treatment with ABC-NP1 also indicated a strong trend for increasing plasma vasopressin levels (FIG. 7). These results demonstrate that the REA amino acid sequence (FIG. 1) in the ring of CNP is responsible for the lack of vasodilatory actions observed with ABC-NP.

Treatment with BC-NP2 did not result in a decrease in mean arterial blood pressure or an increase in renal blood flow (FIGS. 6 and 8). Thus, like ABC-NP, BC-NP2 does not have vasodilatory effects. As compared to ABC-NP, BC-NP2 only had about 50 percent of the renal effects (FIGS. 4 and 5). These results demonstrate that the five amino acid residues of ANP present at the N-terminus of ABC-NP are involved in the prolonged aquaretic and diuretic actions of ABC-NP.

The biological effects of ABC-NP, ABC-NP1, or BC-NP2 on cardiac fibroblast cells were tested in vitro. Briefly, 80-90% confluent cardiac fibroblast cells were incubated in Hank's balanced salt solution (InVitrogen) containing 20 mmol/L N-[2-hydroxyethyl]piperazine-N'[2-ethanesulfonic acid], 0.1% bovine serum albumin, and 0.5 mmol/L 3-isobutyl-1-methylxanthine (Sigma). Treated cells received ANP ($10^{-6}$ M), BNP ($10^{-6}$ M), CNP ($10^{-6}$ M), ABC-NP ($10^{-11}$ M, $10^{-8}$ M, or $10^{-6}$ M), ABC-NP1 ($10^{-11}$ M, $10^{-8}$ M, or $10^{-6}$ M), or BC-NP2 ($10^{-11}$ M, $10^{-8}$ M, or $10^{-6}$ M) for 10 minutes. Cells were lysed in 6% TCA and sonicated for 10 minutes. The samples were ether extracted four times in four volumes of ether, dried, and reconstituted in 300 μL cGMP assay buffer. The samples were assayed using a competitive RIA cGMP kit (Perkin-Elmer, Boston, Mass.). Briefly, samples and standards were incubated with 100 μL anti-human cGMP polyclonal antibody and $I^{125}$-antigen for 18 hours. cGMP assay buffer was added to the samples, and they were centrifuged for 20 minutes at 2500 rpm. The free fraction was aspirated off; the bound fraction was counted; and concentrations determined Samples were corrected for dilution factors, and values were expressed as pmoles/mL. There is no cross-reactivity with ANP, BNP, or CNP, and there is <0.001% reactivity with cAMP, GMP, GDP, ATP, and GTP.

Figure 9:
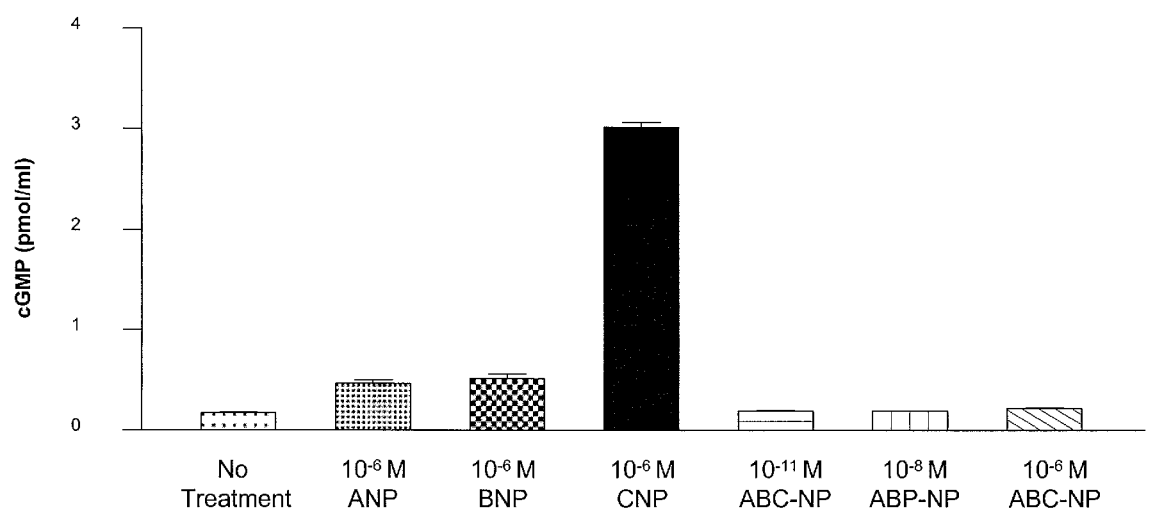
FIG. 9 is a bar graph plotting the level of cGMP (pmol/mL) in untreated human cardiac fibroblasts and human cardiac fibroblasts treated with ANP ($10^{-6}$ M), BNP ($10^{-6}$ M), CNP ($10^{-6}$ M), ABC-NP ($10^{-11}$ M, $10^{-8}$ M, or $10^{-6}$ M), or ABC-NP+BNP ($10^{-6}$ M each) for 10 minutes.
Figure 10:
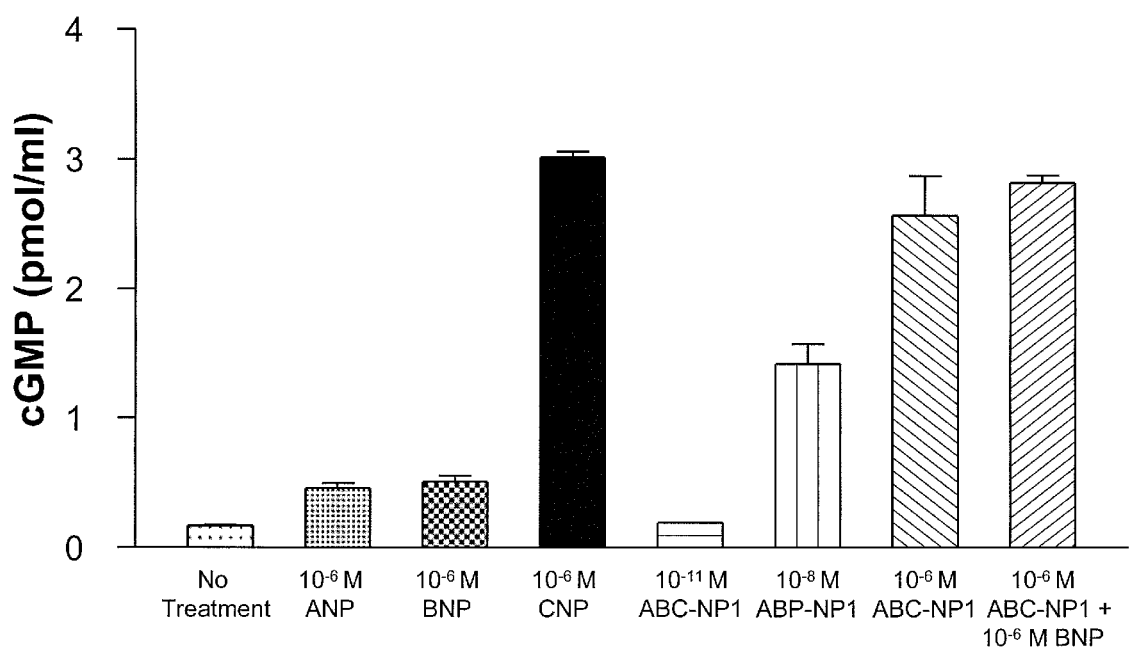
FIG. 10 is a bar graph plotting the level of cGMP (pmol/mL) in untreated human cardiac fibroblasts and human cardiac fibroblasts treated with ANP ($10^{-6}$ M), BNP ($10^{-6}$ M), CNP ($10^{-6}$ M), ABC-NP1 ($10^{-11}$ M, $10^{-8}$ M, or $10^{-6}$ M), ABC-NP1+BNP ($10^{-6}$ M each) for 10 minutes.
Figure 11:
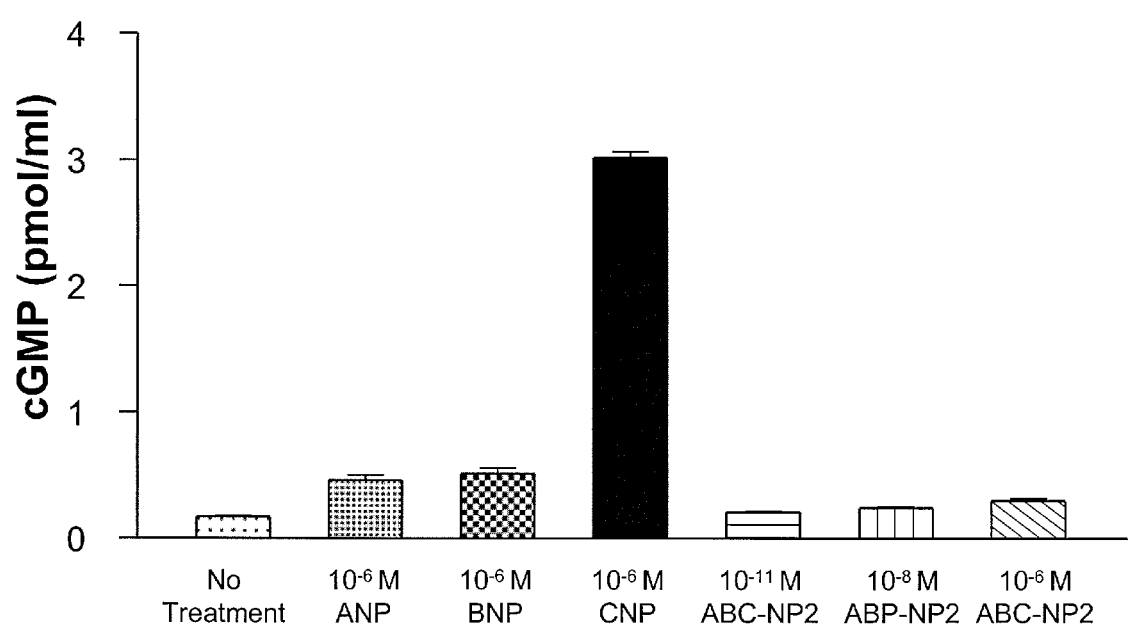
FIG. 11 is a bar graph plotting the level of cGMP (pmol/mL) in untreated human cardiac fibroblasts and human cardiac fibroblasts treated with ANP ($10^{-6}$ M), BNP ($10^{-6}$ M), CNP ($10^{-6}$ M), or BC-NP2 ($10^{-11}$ M, $10^{-8}$ M, or $10^{-6}$ M) for 10 minutes.

Treatment with ABC-NP1 activated cGMP in human cardiac fibroblasts, while treatment with ABC-NP and BC-NP2 did not (FIGS. 9-11). These results demonstrate that ABC-NP1 has biological effect in human cardiac fibroblasts, while both ABC-NP and BC-NP2 do not appear to have any biological effects in human cardiac fibroblasts. Thus, ABC-NP1 may have the ability to induce anti-fibrotic actions, which may not be present with ABC-NP or ABC-NP2.

Example 2

Biological Effects of ABC-NP, ABC-NP1, and BC-NP2 Polypeptides Using Animal Models The effects of ABC-NP, ABC-NP1, or BC-NP2 infusion is further assessed in two large animal models of sodium retention: the paced dog model of CHF and a dog model of sodium retention which mimics cirrhosis and nephrosis. The first model is the rapid pacing model of CHF as described elsewhere (Chen et al., *Circulation*, 100:2443-2448 (1999)). Briefly, dogs are paced at 240 bpm for 10 days to generate a model of severe CHF. Twenty-four dogs are paced, six receive ABC-NP polypeptides, six receive ABC-NP1 polypeptides, six receive BC-NP2 polypeptides, and six receive lasix (as diuretic control). Acute hemodynamic studies are performed at the time of infusion and comparisons are made between groups and among dogs at baseline and infusion. The second model is the TIVCC model of sodium-retention and ascites without concurrent increases in cardiac filling pressure as described elsewhere (Wei et al., *Am. J. Physiol.*, 273:R838-844 (1997)). The ABC-NP, ABC-NP1, and BC-NP2 polypeptides are tested in each dog model of sodium-retention using increasing doses up to 100 pmol.kg/minute administered intravenously.

Example 3

Treating Patients at Risk of Left Ventricular Remodeling

Patients (e.g., myocardial infarction patients) at risk of left ventricular remodeling are treated with IV infusions of ABC-NP1 polypeptide. Prior to the infusion, vital signs are taken and laboratory tests are performed to measure neurohormones and renal function. MRI is done to measure left ventricular size and function. An intravenous infusion of ABC-NP1 polypeptide is initiated at a dose of between 0.001 μg/kg/minute and 1 μg/kg/minute. Vital signs are assessed every two hours during the infusion. The infusion can last for 72 hours. Blood is drawn before the infusion is stopped at 72 hours to measure neurohormones and renal function. Patients return in one month and six months for repeat MRI to assess left ventricular size and function.

Example 4

Treatment of Cardiorenal Conditions

Patients who develop worsening renal function with diuretic resistance in the setting of acute decompensated heart failure are treated prospectively with IV infusions of ABC-NP or BC-NP polypeptides. Prior to the infusion, vital signs are taken and laboratory tests are performed to measure electrolytes, serum creatinine, cystatin, and BNP polypeptide levels. Baseline urine output is measured and urine electrolytes are assessed. An intravenous infusion of ABC-NP or BC-NP polypeptides is initiated. Vital signs and urine output are assessed every 2 hours during the infusion, which is 12 to 72 hours in duration. Drug levels (e.g., ABC-NP or BC-NP polypeptide levels), BNP polypeptide levels, serum creatinine, cystatin, and plasma and urine electrolytes are assessed daily throughout the infusion.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A natriuretic polypeptide less than 45 amino acid residues in length, wherein said polypeptide comprises, in an order from amino terminus to carboxy terminus:
    (a) the sequence set forth in SEQ ID NO:1 or the sequence set forth in SEQ ID NO:1 with no more than one mismatch,
    (b) the sequence set forth in SEQ ID NO:7 or the sequence set forth in SEQ ID NO:7 with no more than two mismatches, and
    (c) the sequence set forth in SEQ ID NO:3 or the sequence set forth in SEQ ID NO:3 with no more than one mismatch, and wherein the said polypeptide has natriuretic activity.

2. The polypeptide of claim 1, wherein said polypeptide comprises the sequence set forth in SEQ ID NO:1.

3. The polypeptide of claim 1, wherein said polypeptide comprises the sequence set forth in SEQ ID NO:7.

4. The polypeptide of claim 1, wherein said polypeptide comprises the sequence set forth in SEQ ID NO:3.

5. The polypeptide of claim 1, wherein said polypeptide comprises the sequence set forth in SEQ ID NO:1, the sequence set forth in SEQ ID NO:7, and the sequence set forth in SEQ ID NO:3.

6. The polypeptide of claim 1, wherein said polypeptide is a substantially pure polypeptide.

7. The polypeptide of claim 1, wherein said polypeptide comprises the sequence set forth in SEQ ID NO:6.

8. The polypeptide of claim 1, wherein said polypeptide consists of the sequence set forth in SEQ ID NO:6.

9. An isolated nucleic acid encoding a natriuretic polypeptide less than 45 amino acid residues in length, wherein said polypeptide comprises, in an order from amino terminus to carboxy terminus:
    (a) the sequence set forth in SEQ ID NO:1 or the sequence set forth in SEQ ID NO:1 with no more than one mismatch,
    (b) the sequence set forth in SEQ ID NO:7 or the sequence set forth in SEQ ID NO:7 with no more than two mismatches, and
    (c) the sequence set forth in SEQ ID NO:3 or the sequence set forth in SEQ ID NO:3 with no more than one mismatch, and wherein the said polypeptide has natriuretic activity.

10. A vector comprising a nucleic acid encoding a natriuretic polypeptide less than 45 amino acid residues in length, wherein said polypeptide comprises, in an order from amino terminus to carboxy terminus:

(a) the sequence set forth in SEQ ID NO:1 or the sequence set forth in SEQ ID NO:1 with no more than one mismatch,
(b) the sequence set forth in SEQ ID NO:7 or the sequence set forth in SEQ ID NO:7 with no more than two mismatches, and
(c) the sequence set forth in SEQ ID NO:3 or the sequence set forth in SEQ ID NO:3 with no more than one mismatch and wherein the said polypeptide has natriuretic activity.

11. A host cell comprising a nucleic acid encoding a natriuretic polypeptide less than 45 amino acid residues in length, wherein said polypeptide comprises, in an order from amino terminus to carboxy terminus:
(a) the sequence set forth in SEQ ID NO:1 or the sequence set forth in SEQ ID NO:1 with no more than one mismatch,
(b) the sequence set forth in SEQ ID NO:7 or the sequence set forth in SEQ ID NO:7 with no more than two mismatches, and
(c) the sequence set forth in SEQ ID NO:3 or the sequence set forth in SEQ ID NO:3 with no more than one mismatch and wherein the said polypeptide has natriuretic activity.

12. The host cell of claim 11, wherein said host cell is a eukaryotic host cell.

13. A pharmaceutical composition comprising a pharmaceutically acceptable carrier and 1 natriuretic polypeptide less than 45 amino acid residues in length, wherein said polypeptide comprises, in an order from amino terminus to carboxy terminus:
(a) the sequence set forth in SEQ ID NO:1 or the sequence set forth in SEQ ID NO:1 with no more than one mismatch,
(b) the sequence set forth in SEQ ID NO:7 or the sequence set forth in SEQ ID NO:7 with no more than two mismatches, and
(c) the sequence set forth in SEQ ID NO:3 or the sequence set forth in SEQ ID NO:3 with no more than one mismatch and wherein the said polypeptide has natriuretic activity.

14. A method for increasing natriuretic activity within a mammal, wherein said method comprises administering to said mammal a natriuretic polypeptide less than 45 amino acid residues in length, wherein said polypeptide comprises, in an order from amino terminus to carboxy terminus:
(a) the sequence set forth in SEQ ID NO:1 or the sequence set forth in SEQ ID NO:1 with no more than one mismatch,
(b) the sequence set forth in SEQ ID NO:7 or the sequence set forth in SEQ ID NO:7 with no more than two mismatches, and
(c) the sequence set forth in SEQ ID NO:3 or the sequence set forth in SEQ ID NO:3 with no more than one mismatch and wherein the said polypeptide has natriuretic activity.

\* \* \* \* \*